United States Patent
Kusch et al.

(10) Patent No.: US 7,776,778 B2
(45) Date of Patent: Aug. 17, 2010

(54) HYDROCARBON CONVERSION CATALYST AND METHODS FOR MAKING AND USING IT

(76) Inventors: Sergey Dmitrievich Kusch, pr. Institutsky, 2-106, Chernogolovka, Moskovskaya obl. (RU) 142432; Sergey Viktorovich Kusnetsov, ul. Krzhizhanovskogo, 3-5-231, St. Petersburg (RU) 193231; Aleksey Jurievich Modnev, ul. Demyana Bednogo, 1-1-121, St. Petersburg (RU) 195274

( * ) Notice: Subject to any disclaimer, the term of this patent is extended or adjusted under 35 U.S.C. 154(b) by 1310 days.

(21) Appl. No.: 11/192,350

(22) Filed: Jul. 28, 2005

(65) Prior Publication Data

US 2006/0060507 A1 Mar. 23, 2006

Related U.S. Application Data

(63) Continuation of application No. PCT/RU2004/000018, filed on Jan. 16, 2004, and a continuation of application No. PCT/RU2004/000017, filed on Jan. 16, 2004.

(51) Int. Cl.
 *B01J 21/18* (2006.01)
 *C10G 25/00* (2006.01)
(52) U.S. Cl. .................... 502/180; 208/299
(58) Field of Classification Search .......... 423/445 B; 502/180, 416–438; 208/299

See application file for complete search history.

(56) References Cited

U.S. PATENT DOCUMENTS

| 5,013,423 A | | 5/1991 | Chen et al. |
| 5,227,038 A | * | 7/1993 | Smalley et al. .............. 204/173 |
| 5,300,203 A | * | 4/1994 | Smalley ................. 204/157.41 |

(Continued)

FOREIGN PATENT DOCUMENTS

FR 2 710 049 3/1995

(Continued)

OTHER PUBLICATIONS

Kushch, S.D. et al. C6+ alkanes dehydrocyclization as addition to reforming process. Oil Processing and Petrochemistry—2005 International Scientific-Experimental Conference. May 25, 2005, Ufa, Russia.*

(Continued)

*Primary Examiner*—Stanley S. Silverman
*Assistant Examiner*—Daniel C. McCracken
(74) *Attorney, Agent, or Firm*—Houston Eliseeva, LLP

(57) ABSTRACT

X-ray amorphous carbon is formed by evaporating carbonic material. The evaporation of carbonic material is conducted in a helium atmosphere at a supply energy flow in the range of 50 to 300 W/mm². The energy is generated, for example, by means of an electric arc. The X-ray amorphous carbon has a starting temperature of an air oxidation, $T_{so}$, $\leq 320°$ C.; a temperature of maximal rate of an air oxidation, $T_{omr}$, $\leq 590°$ C.; a temperature of end of an air oxidation, $T_{eo}$, $\leq 630°$ C.; an initial rate of non-catalytic hydrogenolysis by molecular hydrogen at 700° C., $V_{hin}$, $\geq 2.08\%$ mass of carbon/h. Upon contact in a solution, 1 g of X-ray amorphous carbon consumes an amount equal to or greater than 16 mmole of $MnO_4^-$ ions. Catalysts based on the X-ray amorphous carbon are used in hydrocarbon dehydrogenation and dehydrocyclization reactions.

30 Claims, 2 Drawing Sheets

U.S. PATENT DOCUMENTS

| | | | |
|---|---|---|---|
| 5,336,828 A * | 8/1994 | Malhotra et al. | 585/654 |
| 5,378,350 A | 1/1995 | Zimmermann et al. | |
| 5,420,371 A * | 5/1995 | Malhotra et al. | 585/266 |
| 5,523,504 A * | 6/1996 | Itoh | 585/452 |
| 5,688,395 A | 11/1997 | Carrazza et al. | |
| 5,688,741 A | 11/1997 | Carrazza et al. | |
| 2003/0044342 A1 * | 3/2003 | Alford et al. | 423/445 R |

FOREIGN PATENT DOCUMENTS

| | | |
|---|---|---|
| GB | 1009511 | 11/1965 |
| RU | 1352707 | 7/1996 |
| RU | 97107731 A | 5/1999 |
| RU | 2 152 977 C1 | 7/2000 |
| RU | 1021124 A1 | 7/2000 |
| RU | 2 157 730 C1 | 10/2000 |
| RU | 677168 A1 | 4/2001 |
| RU | 492115 A1 | 1/2002 |
| WO | 90/06907 A1 | 6/1990 |

OTHER PUBLICATIONS

Kushch, S.D. et al. C6+ alkanes dehydrocyclization as addition to reforming process. 7th International Petrochemical Process Intensification Conference "Petrochemistry-2005", 2005, Nizhnekamsk, Tatarsta.*

English Translation of Russian Patent Publication No. 97107731 A, published May 20, 1999.

Moldavskii, B. et al., Zhurnal Obshchei Khimii, 1937, b. 7, No. 13, pp. 1840-1847.

Shuikin, N.I. et al., "A Pentamerous Cyclenes Dehydrogenation in the Presence of Activated Carbon," Doklady Akademii Nauk SSSR, 1960, b. 135, No. 1, pp. 105-108.

English Translation of International Preliminary Report on Patentability, dated Sep. 2, 2005, from International Application No. PCT/RU2004/000017, filed Jan. 16, 2004.

International Search Report, mailed Apr. 15, 2004, from International Application No. PCT/RU2004/000017, filed Jan. 16, 2004.

International Search Report, mailed Apr. 29, 2004, from International Application No. PCT/RU2004/000018, filed Jan. 16, 2004.

Kushch, S.D. et al. C6+ alkanes dehydrocyclization as addition to reforming process. 7th International Petrochemical Process Intensification Conference "Petrochemistry-2005", 2005, Nizhnekamsk, Tatarstan.

Matthews, C.K. et al., "Vapour pressure and enthalpy of sublimation of C70," Fullerene Science and Technology, 1993, pp. 101-109, vol. 1(1), Marcel Drekker, Inc., USA.

Sanford, R. A. et al., "Reforming with Carbon Catalysts," Industrial and Engineering Chemistry, Dec. 1954, pp. 2568-2571, vol. 46, No. 12, American Chemical Society, USA.

Trunschke, A. et al., "Transition metal oxide/carbon composite catalysts for n-alkane aromatization: structure and catalytic properties," Applied Catalysis A: General, 2001, pp. 382-392, vol. 208, Elsevier Science.

* cited by examiner

HYDROCARBON CONVERSION CATALYST AND METHODS FOR MAKING AND USING IT

RELATED APPLICATIONS

This application is a Continuation of PCT application serial number PCT/RU2004/000018 filed on Jan. 16, 2004 which claims priority to RU2003103728 filed on Jan. 31, 2003 and PCT application serial number PCT/RU2004/000017 filed on Jan. 16, 2004 which claims priority to RU2003103727 filed on Jan. 31, 2003 all of which are incorporated herein by reference in their entirety.

BACKGROUND OF THE INVENTION

Both dehydrogenation and dehydrocyclization processes include C—H bond activation and subsequent cleavage. The rather strong C—H bond activation is an a priori difficult problem. In a hydrocarbon molecule there are present several C—H bonds and as all C—H bonds are approximately equivalent in bond energy, it is difficult obtain high selectivity in dehydrogenation and dehydrocyclization reactions. The alkenes generated during dehydrogenation undergo further dehydrogenating conversions to form condensation products which are poor in hydrogen content. These products are precursors of carbonaceous deposits usually referred to as "coke". Coke deposition deactivates the catalyst; therefore its activity and selectivity change over time. Preventing coke formation is one of the main problems in hydrocarbon processing.

Because of active coking, both dehydrogenation and dehydrocyclization as conventional reforming processes are carried out at feed dilution by hydrogen or steam at evident preponderance of diluent (molar proportion is up to 5:1). The effect of this diluent probably consists in elimination of freshly formed coke as a result of its hydrogenation or steam conversion. Feed dilution, i.e. low feed concentration, in reaction the zone decreases the degree of conversion and requires an increase of contact time, for example by pressure increase in the reaction apparatus. Increased hydrogen pressure decreases the amount of coke that is deposited but promotes hydrocracking and hydrogenolysis side reactions. An undesirable effect of both the increase in total pressure and in hydrogen pressure is the decrease of both dehydrogenation and dehydrocyclization reactions, as reactions that are carried out with increase of particles number and with hydrogen elimination. In real reforming processes at the most 15-20% of alkanes in feed are converted. Besides, reforming feed undergoes additional pretreatment for removal of: catalytic poisons (usually sulfur compounds); unconverted pentanes; and alkenes deactivating of catalyst.

A catalyst of dehydrogenation and dehydrocyclization of alkanes containing aluminum chromate (5-60 mass % in recalculation on $Cr_2O_3$) on the support (see Patent of Russian Federation No. 492115, Intern'l Class B01J 23/26, published Jan. 27, 2002) is known.

Shortcomings of this known catalyst are the considerable feedstock losses on coking and gas (hydrogen and light hydrocarbons).

The method of preparation of the catalyst of alkanes dehydrogenation and dehydrocyclization included deposition of active phase in the form of aluminum chromate on preliminary calcined alumina, or on a product of hydrargillite dehydration (see patent of Russian Federation No. 677168, Intern'l Class B01J 21/04, $CO_7C$ 5/32, is published Apr. 10, 2001).

The use of the catalyst prepared by this known method, results, as stated above, in considerable losses of feedstock on coking and gas.

A catalyst of hydrocarbons conversion including in % mass: nickel oxide 10.5-13.5; oxide of titanium 0.2-0.6; oxide of boron 0.3-0.9 and alumina—the rest (see Patent of Russian Federation No. 2157730, Intern'l Class B01J 37/02, B01J 23/755, published Oct. 20, 2000) is known.

Shortcomings of this known catalyst lie in the major losses of feedstock, undesirable formation of coke and light hydrocarbons, sensitivity to sulfur compounds and impossibility to use it in alkene-containing feed.

The method of preparation of this catalyst of hydrocarbons conversion is based in impregnation of the support in solution of nickel and aluminum nitrates and calcination of catalyst mass at 400-500° C. The support is prepared by molding of mixture including alumina, titanium hydride, boric acid and technical carbon with addition of mixture of paraffin, wax and oleinic acid as a binder, by casting at overpressure 0.4-0.2 mPa and temperature 70-75° C. with subsequent sun-curing and calcination (see Patent of Russian Federation No. 2157730, Intern'l Class B01J 37/02, B01J 23/755, published Oct. 20, 2000).

At hydrocarbons conversion over this catalyst prepared by the known method, considerable feed losses on formation of coke and gas, catalyst deactivation by formed coke and decrease of an inter-regeneration cycle is observed.

Carbon based catalysts for C—H bond activation have not been extensively studied. B. L. Moldavskii with coworkers found catalytic activity of carbon materials, specifically activated carbon and coke, in dehydrocyclization of n-octane or diisobutyl (2.5-dimethylhexane) and cyclohexane dehydrogenation at temperature of 500 to 560° C. and liquid hourly space velocity (LHSV) 0.1-0.15 $h^{-1}$. In addition to this reactions, cycloalkane cracking actively occurred (see B. Moldavskii, F. Bezprozvannaya, G. Kamusher and M. Kobyl'skaya, Zhurnal Obshchei Khimii, 1937, b. 7, No. 13, p.p. 1840-1847).

Shortcoming of the known catalyst is the low activity, which is further slowed down during processing time, likely in connection with coke formation. The feedstock dilution by hydrogen does not inhibit of coking.

One of this catalysts is coke produced by pyrolysis of straight-run gasoline at 600° C. (see B. Moldavskii, F. Bezprozvannaya, G. Kamusher and M. Kobyl'skaya, Zhurnal Obshchei Khimii, 1937, b. 7, No. 13, p.p. 1840-1847).

A known catalyst for reforming of naphta, which consisted of petroleum hydrocarbons having more than 6 carbon atoms and not containing alkenes, was represented by activated carbon without treatment or one after impregnation in carbonates or hydroxides of alkali metals (Na, K, Li) and was used at temperature range 538-593° C. The treatment of activated carbon by carbonates and hydroxides of alkali metals decreased coking velocity and enabled catalyst regeneration (see R. A. Sanford and B. S. Friedman, Reforming with Carbon Catalysts, Ind. Eng. Chem., 1954, v.46, No. 12, p.p. 2568-2571).

The shortcoming of this known catalyst include low (not more than 20%) conversion grade, poor activity of treated catalyst in dehydrogenation reaction (the toluene yield from methylcyclohexane is 15.1%) and in dehydrocyclization process (toluene yield from n-heptane is 9.6%) and impossibility of inhibiting coking. So, at the feed dilution by hydrogen or steam at the molar proportion of diluent/hydrocarbon equal to 2.4, feed losses are equal to 2.3% by mass.

The entire carbon based catalyst rapidly lose activity with increased space velocity that is connected with coking and decrease of catalyst specific surface (see N. I. Shuikin, T. I. Naryshkina, Doklady Akademii Nauk SSSR, 1960, b. 135, No. 1, p.p. 105-108).

A catalyst for aromatization of n-hexane and n-octane based on composition of $ZrO_2$ and carbon, prepared by sol-gel technique (see H. Preiss, L.-M. Berger, K. Szulzewsky.—Carbon. —1996, V.34, No. 1, p. 109-119) with subsequent calcination at different temperatures in He atmosphere is known. The most preferred catalyst sample with respect to catalytic activity was characterized by specific surface 141 $m^2/g$, hydrogen adsorption (desorption) 92-93 μmole/g and ammonia desorption 0.21 mmole/g.

The aromatization of n-hexane and n-octane over this known catalyst was carried out only in hydrogen but not nitrogen atmosphere. n-Hexane conversion grade at its aromatization amounted to 20.7%, selectivity with respect to benzene—66.7%. The comparable amounts of alkane $C_1$-$C_4$ and alkene $C_2$-$C_4$, methylpentenes and methylcyclopentene in gas phase were observed. n-Octane conversion occurred more actively: conversion grade amounts to 35.5%, selectivity with respect to aromatics consisting mainly in comparable amounts of ethylbenzene and xylene was equal 91.2% (see D. L. Hoang, H. Preiss, B. Parlitz, F. Krumeich, H. Lieske, Appl. Catal. A. General, 1999, V.182, N 2, P. 385-397; A. Trunschke, D. L. Hoang, J. Radnik, K.-W. Brzezinka, A. Bruckner, H. Lieske, Appl. Catal. A. General, 2001, V.208, N2, P. 381-392).

The shortcomings of this known catalyst are its low (not more than 35.5%) alkane conversion grade, necessity of feed dilution by hydrogen in view of coking and impossibility of its use for aromatization of cyclohexane and its homologs.

Catalytic cracking, mainly with formation of alkane $C_1$-$C_4$ and alkene $C_2$-$C_4$ and n-octane isomerization occurred on a catalyst calcined at high temperature and containing zirconium oxycarbonyl.

It is necessary to point that carbonic catalysts are operated as a rule at higher (>500° C.) temperatures than those for known industrial reforming catalyst (450-470° C.) and have low isomerization activity.

A catalyst for dehydrogenation and hydrogenation of hydrocarbons including hydrogenolysis accepted as prototype based on fullerenes of the common formula $C_n$, where n=50-120, has been known. The catalyst is dissolved in a feed or dissolved in an appropriate solvent (see U.S. Pat. No. 5,336,828, Intern'l Class C07C 5/327, US Class 585/654, is published Aug. 9, 1994; U.S. Pat. No. 5,420,371, Intern'l Class C07C 005/03; C07C 005/10, US Class 585/266, published May 30, 1995).

The method of production of catalyst based on fullerene mixture included evaporation of carbon or graphite in the chamber at inert gas pressure 200 Torr by means of ohmic heat and concentrated solar radiation to surface temperatures 3000 to 4000° C., fullerene soot collection from chamber wall or its evacuation from inert gas and subsequent extraction of fullerene from fullerene soot by organic solvent accepted as prototype is known (see Patent of France 2710049, Inter'l Class C01B 31/00, is published Mar. 24, 1995).

The use of this catalyst in a solution inhibits insoluble products formation specifically coke. This known catalyst is active only in dehydrogenation of hydroaromatics but not that of alkanes. The applicability of the known catalyst for dehydrogenation of cyclohexane and its homologs is unknown, which makes the use of the known catalyst for alkane dehydrocyclization near to impossible. The fullerene sublimation decreased the usable temperature of known catalyst. The formation of stable fullerene hydride places in doubt the possibility of dehydrogenation of hydroaromatics with high conversion grade. The experiments show that fullerene and its epoxides catalyze alkane cracking but not alkane dehydrogenation.

Process of conversion of n-hexane to benzene over $Cr_2O_3$—$Al_2O_3$—$Na_2O$ catalyst in temperature range 550-580° C., pressure range 300-1500 Torr, hydrogen/hydrocarbon molar proportion equal to 3/1 and liquid hourly space velocity of feed in the range 0.2-2.0 $h^{-1}$ is known (see Patent of Great Britain 1009511, Intern. Class C07C 5/00, is published Nov. 10, 1965).

The known method shortcomings are need of feed delution by hydrogen, low feed conversion degree, big feed dissipation on coke and gas that amount to 15.3%, concerned with that catalyst deactivation and increase of its activity that overcome by process temperature increase.

The process of petroleum feed processing (see U.S. Pat. No. 5,013,423, Intern. Class C10G 35/06, is published May 7, 1991) wherein the feed is contacted with non-acid dehydrogenation catalyst in hydrogen presence at the process condition (temperature, pressure and feed space velocity) that suffices for dehydrocyclization is known. The catalyst contains metal of platinum group on zeolite support with ZSM-5 type structure containing of indium. The product obtained at process temperature more than 427° C. in hydrogen presence have both more high octane number and aromatics content than initial reforming feed.

The known process shortcomings is low feed conversion degree, high benzene content (25-30%) in the end product, catalyst coking and needs of feed delution by hydrogen.

The process of pentane fraction processing with production of liquefied petroleum gas at direct interaction over acidic crystalline aluminosilicate with silicate module more than 12 having peak temperature of hydrazin desorption more than 650° C. (see Japan Patent by application No 3-54717, Intern. Class C10G May 11, 1993) is known.

The known process shortcomings are need of separation and utilization of by-products obtained in amount up to 12 vol. % and progressive catalyst coking with variable during process time products content and absence of dehydrogenation, dehydrocyclization or cracking of feed.

The process of conversion of heavy hydrocarbon (see RF Application 97107731, Intern. Class C10G 47/32, B01J 23/78, is published May 20, 1999) inclusive a supply of heavy hydrocarbon feed into reaction zone and feed conversion over catalytically active phase. Catalytically active phase includes first metal (not noble metal of group VIII) and second metal (alkali metal). The contacting of initial feed with a steam at a pressure ≦2.1 mPa to produce hydrocarbons with decreased boiling temperature is realized in the known process. The first metal is selected from group include iron, cobalt, nickel or mixture of it, second metal is selected from group composed of potassium, sodium or its mixture. At least one from metals is fixed on support. The support is mesoporous, selected from group composed of silica, natural or synthetic aluminosilicates, aluminium oxides, petroleum cokes, coals or carbon base material obtained from vegetable or animal substance.

The known process shortcomings are feed cracking, the need of its delution, steam conversion of feed with syngas formation, progressive coking and catalyst deactivation concerned with that.

The process of processing of hydrocarbon feed based on aliphatic hydrocarbons (see RF Patent 2152977, Intern. Class C10G 35/095, is published Jul. 20, 2000) inclusive a supply of feed into reaction zone, delution of it by hydrocarbon gas and process realization at elevated temperature in preference 320-420° C. over silica-alumina catalyst with subsequent separation of end products. Aluminocobaltmolybdenic zeolite-containing catalyst with composition (in % mass.) zeolite ZSM-11 (silicate module is 17-60) 15÷45, cobalt oxide 2÷6, molibdenum oxide 8÷14 and a binder as catalyst is used. Sweet natural gas is used as hydrocarbon gas-deluent and process carries out at pressure 1.5-2.0 mPa to produces catalysate inclusive end aromatics and $C_1$-$C_5$ hydrocarbons with subsequent isolation of hydrocarbon fraction used as addition elevating gasoline octane number or high octane gasoline and liquefied $C_3$-$C_4$ hydrocarbons.

The known process shortcomings are the need of insertion of deluent natural gas with its previous pretreating (desulfurization or hydrofining) that complicates of process, high pressure of process carried out with particles number increase that causes feed conversion degree decrease, the need of pentanes removal from feed, the impossibility of conversion of alkenes and cycloalkanes or feed inclusive it and catalyst susceptibility to sulfur compounds conventional poisons.

The process of reforming of naphta consisted of petroleum hydrocarbons having more than 6 carbon atoms and not containing alkenes contained in the use activated carbon without treatment or one after impregnation in carbonates or hydroxides of alkali metals (Na, K, Li) as the catalyst at temperature range 538-593° C., is known. The treatment of activated carbon by carbonates and hydroxides of alkali metals decreases coking velocity and enable catalyst regeration (see R. A. Sanford and B. S. Friedman, Reforming with Carbon Catalysts, Ind. Eng. Chem., 1954, v.46, No. 12, pp. 2568-2571). The shortcoming of known process are low (not more than 20%) conversion grade, poor activity of treated catalyst in dehydrogenation reaction (the toluene yield from methylcyclohexane is 15.1%) and in dehydrocyclization process (toluene yield from n-heptane is 9.6%) and impossibility of coking inhibiting. So, at the feed delution by hydrogen or steam at the molar proportion diluent/hydrocarbon equal to 2.4 feed losses is equal 2.3% mass.

The process of dehydrogenation and hydrogenation of hydrocarbons including hydrogenolysis accepted as prototype (U.S. Pat. No. 5,336,828, Intern. Class C07C 5/327, is published Aug. 9, 1994) inclusive feed contacting with the catalyst representing at least one dissoluble fullerenes $C_n$, where n=50-120 at reaction mixture thermostating in temperature ranging 25-500° C. and pressure ranging 1-1500 Torr has been known. Named fullerene has been dissolved in the feed if the feed is liquid able to dissolve of fullerene or in additional solvent that is solvent for hydrocarbons too. The use of the catalyst in the form of solution is impeded of coke formation in the known process-prototype.

The shortcoming of known process-prototype are following. The known catalyst is active in hydroaromatics dehydrogenation only but not in alkane hydrogenation. The usefulness of known catalyst for dehydrogenation of cyclohexane and its homologs is unknown that excludes of use of known catalyst for alkane dehydrocyclization. Fullerene sublimation (S. K. Mathews, M. Sai Baba et al. Fullerene Science and Technology. 1993. No 1 (1). P. 101-109; M. V. Korobov, L. N. Sidorov, J. Chem. Termodynamics. 1994. V.26. P. 61-73) decreases temperature of use of known catalyst and constricts the field of reactions that are possible by thermodynamics.

So, both fullerene and its epoxides catalyze the cracking of alkanes but not its dehydrogenation. The formation of stable fullerene hydrides by the heating of mixture of fullerene and hydroaromatics causes of doubt about validity of possibility of dehydrogenation of hydroarmatics with high conversion degree.

SUMMARY OF THE INVENTION

The present invention relates to a hydrocarbon conversion catalyst, a method for producing it and to hydrocarbon conversion processes using the catalyst.

The catalyst of the present invention comprises x-ray amorphous carbon produced by evaporation of carbonic material and having the following characteristics: starting temperature of an air oxidation, $T_{so}$, ≦320° C.; temperature of maximal rate of an air oxidation, $T_{omr}$, ≦590° C.; temperature of end of an air oxidation, $T_{eo}$, ≦630° C.; an initial rate of non-catalytic hydrogenolysis by molecular hydrogen at 700° C., $V_{hin}$, of ≧2.08% mass of carbon/h. At contact in a solution, 1 g of the x-ray amorphous carbon consumes an amount of at least 16 mmole of $MnO_4^-$ ions.

The preferred x-ray amorphous carbon is characterized by temperatures $T_{so}$=280° C. and $T_{omr}$=508° C.

The x-ray amorphous carbon is a finely-dispersed material with particle size of up to 0.04 mm, specific surface, S, from 210 to 280 $m^2$/g, and bulk density, p, ≦0.05 g/$cm^3$.

In addition to the x-ray amorphous carbon, the catalyst can include inert granular material. The catalyst can be produced in the form of granules molded from a mixture of x-ray amorphous carbon and a binder.

The method of production of the catalyst of the invention comprises evaporating carbonic material in a helium atmosphere at a supply energy flow in the range of 50 to 300 W/$mm^2$. Graphite can be used as carbonic material and the evaporation of carbonic material can be carried out by action of laser radiation or by action of an electric arc.

From deposition of fullerene soot formed at evaporation, fullerenes are extracted from the soot by organic solvent. The precipitate is separated, washed and dried. Drying can be conducted in vacuum at a temperature in the range of 150 to 200° C.

The molding of granules is realized, for example, by means of an extrusion of moistened mass with subsequent sun-curing at room temperature and calcination at a temperature range of from 200 to 550° C. in vacuum.

The catalyst is useful in hydrocarbon conversions, namely in reactions that involve hydrocarbon C—H bonds and which result in cleavage of these bonds and formation of compounds containing multiple bonds. Thus the invention also is related to a process for conducting hydrocarbon dehydrogenation and dehydrocyclization reactions and processes in which these reactions take place, in particular dehydrogenation of alkane $C_2$-$C_5$ with alkene formation, of cyclo-$C_5$-alkane to cycloalkenes or cycloalkadienes, of cyclo-$C_6$-alkanes to benzene and its homologs as well as dehydrocyclization of $C_{6+}$-alkanes with formation of benzene and its homologs. The process includes contacting a feed with the catalyst.

The catalyst is particularly active in dehydrogenation of alkanes and cycloalkanes and dehydrocyclization of alkanes and can be used in processes that include not only hydroaromatics but also both alkanes and cycloalkanes, resulting in dehydrogenation of cyclo-C6-alkanes and dehydrocyclization of alkanes. The catalyst does not become deactivated in the processing of pentane and alkenes and does not undergo coking. It does not require transition or noble metals or feed dilution by hydrogen or water stream. Furthermore, the catalyst is not susceptible to catalytic poisoning by sulfur compounds. The catalyst retains its activity generally associated with that of the reforming catalysts and can be used to convert feeds with only 15-20% paraffins.

DETAILED DESCRIPTION OF THE PREFERRED EMBODIMENTS

The present invention relates to a catalyst used for hydrocarbon conversions and methods for producing it. The present invention also relates to processes that employ the hydrocarbon conversion catalyst.

Catalyst

The catalyst of the present invention comprises x-ray amorphous carbon produced by evaporation of carbonic material and having the following characteristics: starting temperature of an air oxidation, $T_{so}$, $\leq$320° C.; temperature of maximal rate of an air oxidation, $T_{omr}$, $\leq$590° C.; temperature of end of an air oxidation, $T_{eo}$, $\leq$630° C.; initial rate of non-catalytic hydrogenolysis by molecular hydrogen at 700° C., $V_{hin}$, $\geq$2.08% mass of carbon/h; and a limiting amount of $MnO_4^-$ ions expended at contact with 1 g of named carbon in the solution$\geq$16 mmole.

The preferred x-ray amorphous carbon is characterized by temperatures $T_{so}$=280° C. and $T_{omr}$=508° C.

The catalyst of the invention, independently of production method, its reactivity and catalytic activity, contains by elemental analysis 95-97% mass of carbon, less than 1.0% of hydrogen and 4-5% of oxygen. Possibly, hydrogen and oxygen are present due to water removal difficulties, since water was detected in absolute methanol after washing of x-ray amorphous carbon that was vacuum-processed at 100° C. for 10 h. The contents of hydrogen and oxygen do not exceed measurement error after one cycle of "deep vacuum at 150° C.—dry air adsorption".

The x-ray amorphous carbon is characterized by high surface area, and has a specific surface area, S, is in the range of 210 to 280 m$^2$/g, depending on production conditions. For comparison, for fine dispersed graphite this value is 6 m$^2$/g.

Figure 1:
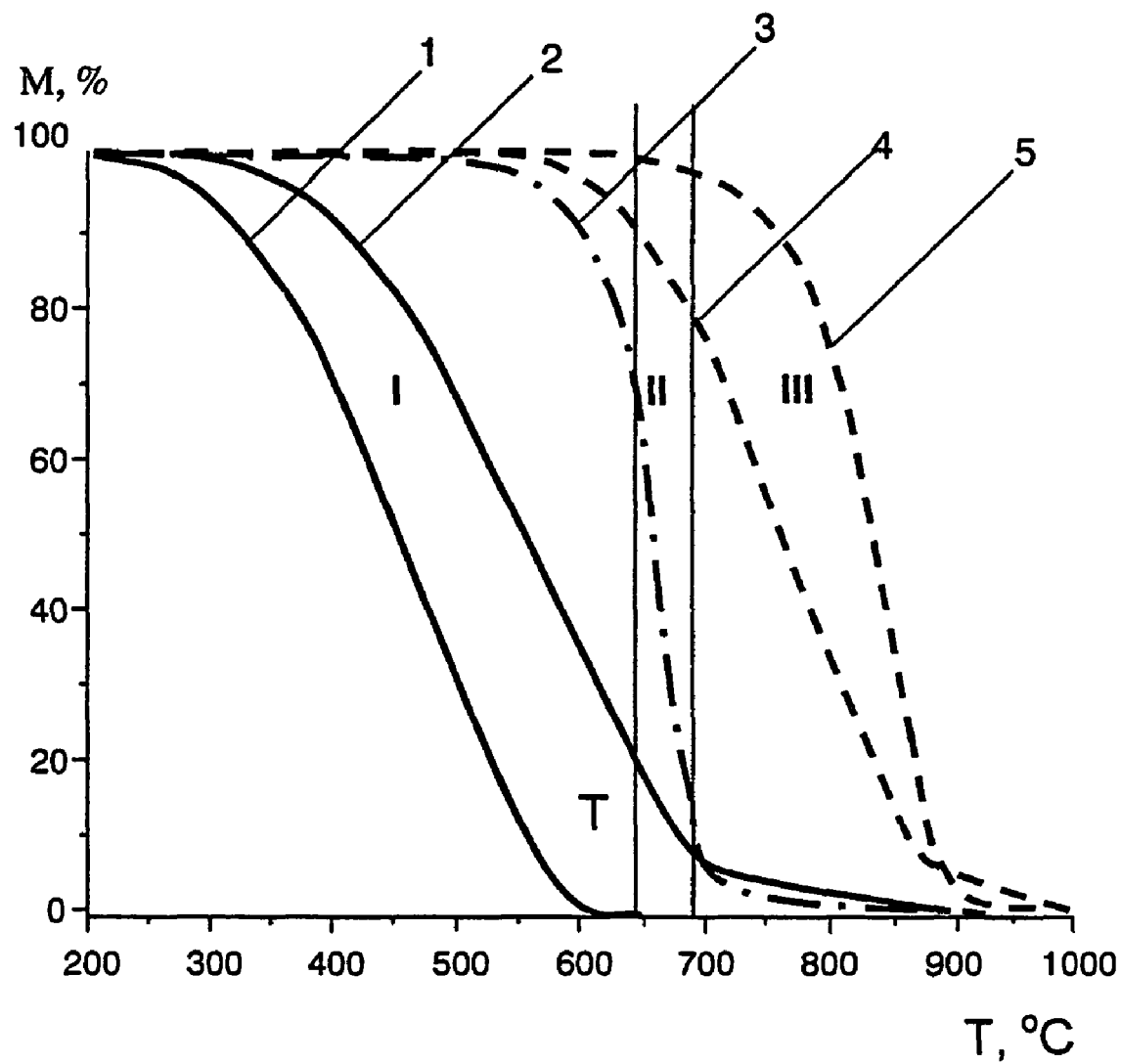
FIG. 1 is a plot of temperature dependence of change of sample mass in air atmosphere for a catalyst having specific surface 210 m$^2$/g, temperatures $T_{so}$=280° C., $T_{omr}$=508° C. and $T_{oe}$=630° C., prepared by evaporation with energy flow 300 W/mm$^2$ (1); for a catalyst having specific surface 210 m$^2$/g, temperatures $T_{so}$=320° C., $T_{omr}$=590° C. and $T_{oe}$=900° C., prepared by evaporation with energy flow 50 W/mm$^2$ (2); for a catalyst prepared at energy flow less than 50 W/mm$^2$ (3); for glassy carbon (4) and graphite (5). Vertical lines note: zone of oxidation of x-ray amorphous carbon (I); zone of oxidation of graphitized particles (II); zone of oxidation of graphite (III).
Figure 2:
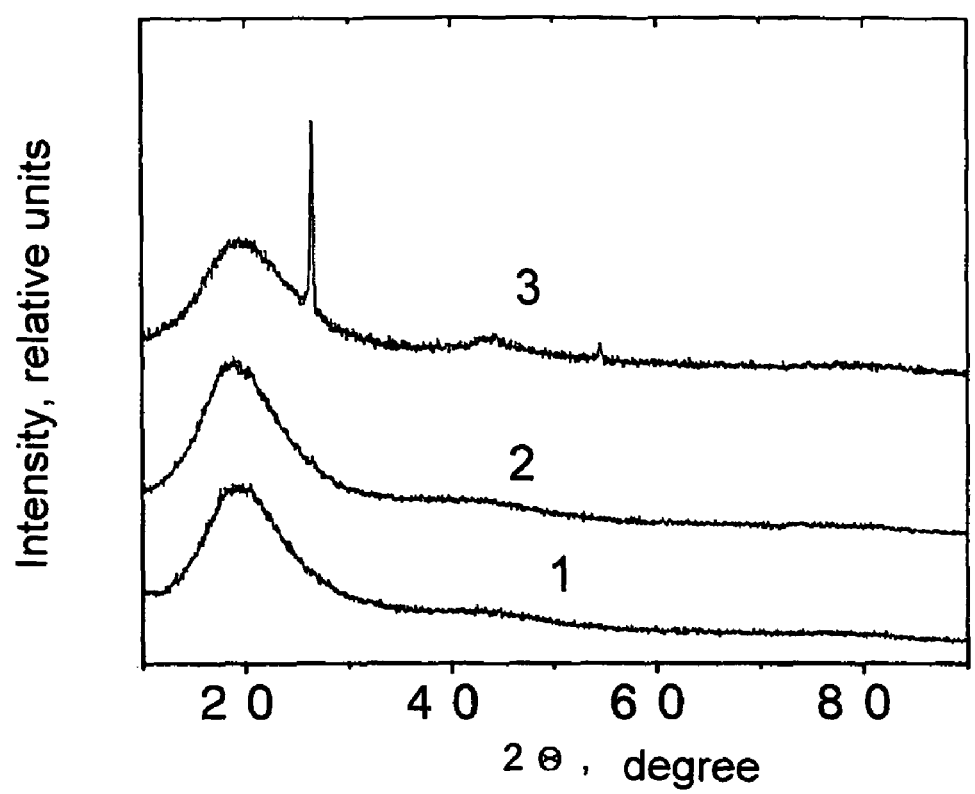
FIG. 2 shows spectra of x-ray diffraction for catalyst (1), catalyst (2) and catalyst (3) (symbols (1), (2) and (3)) of FIG. 1.

If the catalyst is prepared at energy flow less than 50 W/mm$^2$ it can includes unconverted graphite that is detected by slow mass loss at temperature higher than 670° C. and graphitized particles (not completely converted graphite) detectable by mass loss in the temperature range of 645-670° C. (see FIG. 1). Graphite also is determined by sharp line 002 in spectra of x-ray diffraction (see FIG. 2).

The presence of graphitized particles and graphite sharply decreases catalyst reactivity. The catalyst prepared by evaporation of carbonic material at the action of energy flow of 50 to 300 W/mm$^2$ and having high catalytic activity does not contain graphite or graphitized particles, as evidenced by the absence of line 002 of graphite (see FIG. 2) and temperature of end of an air oxidation $T_{eo}$=630° C. (see FIG. 1).

Figure 3:
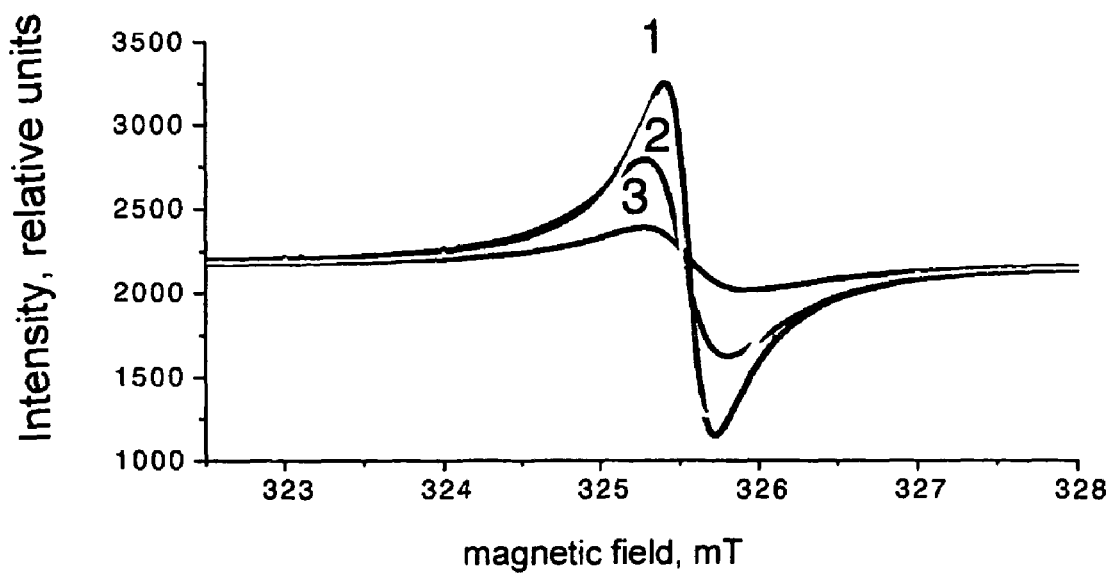
FIG. 3 shows spectra of electron spin resonance (ESR) for catalyst (1), catalyst (2) and catalyst (3) ((symbols (1), (2) and (3)) of FIG. 1.

The ESR spectra of the catalyst in vacuum are represented by a single line with linewidth of 0.19 mT and g-factor 2.0022 (see FIG. 3). This line is similar to a Lorenz curve in the centre and has wide wings. The catalyst contains (2-5)×10$^{20}$ spins on carbon moles, i.e., 1 paramagnetic center per 1000-3000 carbon atoms as determined by second integral of ESR spectra (or area under integral form of line). The paramagnetic centers are defined by defects of the dangling C—C bonds type.

Besides dangling bonds, the catalyst contains multiple non-conjugated C=C bonds. X-ray amorphous carbon, as similar compounds with non-conjugated multiple C=C bonds, interacts with $MnO_4^-$ ions in neutral media (Vagner test reaction), is brominated by solution of $Br_2$ or $(C_4H_9)_4NBr_3$, but does not react with maleic anhydride. Upon contacting the x-ray amorphous carbon of the invention with $MnO_4^-$ ions in neutral solution, a decrease of $MnO_4^-$ ion concentration is observed and $MnO_4^-$ ion consumption in neutral media per 1 g of x-ray amorphous carbon equals or exceeds 16 mmoles. Other carbonic materials, in particular graphite, glassy carbon and activated carbons, do not interact with $MnO_4^-$ ion, i.e. $MnO_4^-$ ion is not consumed when in contact with these other carbonic materials.

The concentration of detectable multiple C=C bonds is much higher than dangling ones. For samples most active in catalysis there is one double bond per 5 carbon atoms.

The claimed catalyst is also characterized by low bulk density (to 0.05 g/cm$^3$). Without mixture with granular material or binder it is suitable for use in static reactors.

The catalyst with addition of inert granular material, for example quartz or ceramics, can be used in the flowing reactor for the avoidance of increase of gas-dynamic resistance or catalyst entrainment with gas flow. If necessary, prepared x-ray amorphous carbon is mechanically mixed with inert granular material, for example with quartz or ceramics with particle size 0.25-1.00 mm in the following proportion: x-ray amorphous carbon 1.65-99.00% by mass and inert granular material the rest.

The use of the catalyst in molded form is preferred. Practically, x-Ray amorphous carbon does not form tough granules upon pressing. The molding of mixture of x-ray amorphous carbon with a binder allows production of tough granules. The gels of hydroxides or hydrogels of metals selected from a group consisting aluminum, magnesium, zirconium titanium or hafnium and mixtures of gels or hydrogels can be used as binder in molding catalysts based on x-ray amorphous carbon, as can be different types of clays.

Aluminosilicates, zeolites and other solid acids contributory to feed cracking and coking on the catalyst are unfit as binders.

The preparation of catalyst granules by extrusion technique is preferred, since prepared extrudate has maximal mechanical reliability and is resistant to abrasion.

The catalyst can be prepare in the form of molded granules of x-ray amorphous carbon and a binder for example neutral gel of hydroxide or neutral hydrogel of metal selected from the group of aluminum, magnesium, zirconium, titanium or hafnium.

The catalyst can consist of 1.65 to 40.00% mass x-ray amorphous carbon with the balance being binder. The mixture of x-ray amorphous carbon and a binder for molding preferably contain 1.65-99.00% mass of x-ray amorphous carbon and the balance, the binder.

The set of above-referenced characteristics of the present catalyst is necessary and sufficient criterion of its activity in the reactions dehydrogenation and dehydrocyclization. The absence of some does not enable attainment of necessary technical effect.

Thus, for example, pyrolytic graphite oxide having $T_{so}$<300° C., but not undergoing hydrogenolysis by molecular hydrogen without catalyst of hydrogen activation even at temperature 700° C., is not active in the reactions of alkanes dehydrogenation and dehydrocyclization. While for other carbonic materials hydrogenolysis is not observed at temperature as high as 1000° C., x-ray amorphous carbon of the invention undergoes hydrogenolysis at temperature $\geq$700° C., in the absence of hydrogen activating catalysts.

Catalyst Preparation

The x-ray amorphous carbon described above is produced by evaporating a feed containing the chemical element of carbon. Graphite is the most preferred carbonic material. The evaporation is conducted in a helium atmosphere and carried out by supplying carbonic material at an energy flow in the range of 50 to 300 W/mm². Electric arc discharge, laser or ultrahigh frequency radiation can be a source of energy flow.

The evaporation products in the form of fullerene soot are deposited, and fullerenes are extracted from the soot by organic solvents, by known technique. Insoluble residue is separated off, washed out by ether and dried.

The evaporation of carbonic material in helium atmosphere can be carried out by electric arc discharge with energy flow of 50 to 300 W/mm² produced in a cylindrical chamber with coaxial electrodes. The proportion of chamber diameter to electrode diameter is in the range of 10:1 to 20:1.

At least one of the electrodes can be made from graphite. In this case voltage with positive polarity is applied on the electrode made from graphite and this electrode is shifted towards the opposite electrode with a shift rate in the range of 0.2 to 6.0 mm/min.

Evaporation of carbonic material is carried out mainly at a helium pressure of 100 to 760 Torr. If the energy flow is less than 50 W/mm², the rate of carbon evaporation and selectivity with respect to x-ray amorphous carbon are significantly less. If the energy flow is higher than 300 W/mm², the selectivity of the evaporation process with respect to x-ray amorphous carbon production is decreased because of an increase of selectivity with respect to both graphized particles and graphite.

More specifically, if the catalyst is prepared at energy flow less than 50 W/mm² it can include unconverted graphite that is detected by slow mass loss at temperature higher than 670° C. and graphitized particles (not completely converted graphite) detectable by mass loss in the temperature range of 645-670° C. (see FIG. 1). Graphite also is determined by sharp line 002 in spectra of x-ray diffraction (see FIG. 2).

The presence of graphitized particles and graphite sharply decreases catalyst reactivity. The catalyst prepared by evaporation of carbonic material at the action of energy flow of 50 to 300 W/mm² and having high catalytic activity does not contain graphite or graphitized particles, as evidenced by the absence of line 002 of graphite (see FIG. 2) and temperature of end of an air oxidation $T_{eo}$=630° C. (see FIG. 1).

Process of electric arc evaporation of graphite is presented as example of carbonic material evaporation. Graphite in the form of cylindrical rod is placed in a cylindrical chamber with a ratio of chamber diameter to evaporated rod diameter being between 10:1 and 20:1. The chamber is filled with helium, preferably at a pressure in the range of 100 to 760 Torr. Energy of direct current with energy flow in the arc is from 50 to 300 W/mm² at a rate of translational movement of evaporated graphite electrode in the range of 0.2 to 6.0 mm/min.

The above indicated process parameters are necessary for generating conditions at which clusters of x-ray amorphous carbon are not deactivated by interaction of one with another. Conveying the graphite electrode more slowly, and more than 300 W/mm² input energy, promote complete atomization of carbon and thermodynamic non-equilibrium state of formed clusters of x-ray amorphous carbon. Clusters of x-ray amorphous carbon formed in the arc and having uncompensated valences, dangling bonds and other reactive fragment of structure are cooled and tempered with preservation of thermodynamic non-equilibrium state during their travel towards and onto cooled chamber walls. At a short way to the chamber walls, i.e., at the proportion of chamber diameter to rod diameter less than 10:1, and inert gas pressure of 100 Torr, i.e. at high concentration of reactive clusters of carbon, frequent collisions of high energy carbon particles lead to interaction of clusters of x-ray amorphous carbon with one another and to closing of uncompensated valences and double bonds, thus promoting formation of product with low reactivity. The evaporable bulk graphite with density in the range of 1.5 to 2.0 g/cm³ is converted to superfine x-ray amorphous carbon with low (less than 0.05 g/cm³) bulk density; therefore long distance to chamber walls and big reacting volume are preferred.

In addition to x-ray amorphous carbon, the catalyst can contain inert granular material for example in the form particles with size of 0.25 to 1.00 mm. This facilitates the convenience of using the catalyst in flow-type apparatus. Quartz or ceramics can be introduced in the catalyst as the inert granular material. The catalyst can consist of 1.65-99.00% mass x-ray amorphous carbon, the balance being inert granular material.

The catalyst can be produced in the form of granules molded from a mixture of x-ray amorphous carbon and a binder.

Neutral gel of hydroxides of a metal selected from a group consisting aluminum, magnesium, zirconium or hafnium can be introduced as a binder.

The mixture of neutral gels of at least two hydroxides of metals selected from group consisting aluminum, magnesium, zirconium or hafnium also can be introduced as a binder. Hydrogel of metal selected from group consisting of aluminum, magnesium, zirconium, or hafnium or a mixture of hydrogels of at least two above-indicated metals can be introduced as a binder. Natural hydrogel can be introduced into catalyst as the hydrogel.

A clay also can be introduced into the catalyst as a binder.

The molding of granules is realized, for example, by means of an extrusion of moistened mass with subsequent sun-curing at the room temperature and calcination at the temperature range of 200 to 550° C. in vacuum. Calcining of the catalyst in air gives rise to oxidation of active x-ray amorphous carbon component. The calcination at a temperature higher than 550° C. is undesirable since available non-conjugated multiple bonds are converted to conjugated aromatic ones, resulting in formation of graphitized particles and decreased catalytic activity.

Hydrocarbon Conversion Processes Using the Catalyst

The catalyst can be used in reactions where it acts on hydrocarbon C—H bonds and contributes to the cleavage of such bonds and formation of compounds containing multiple bonds.

More specifically, the present invention relates to reactions of hydrocarbons conversion, in particular to dehydrogenation and dehydrocyclization of hydrocarbons and to processes where this conversions are accomplished. In particular, the catalyst can be used in dehydrogenations of alkanes $C_2$-$C_5$ with formation of alkenes; of cyclo-$C_5$-alkanes to cycloalkenes or cycloalkadienes; of cyclo-$C_6$-alkanes to benzene and its homologs; and to dehydrocyclization of $C_{6+}$ alkanes with formation of benzene and its homologs.

An object to be solved by the claimed invention is working out the process of hydrocarbons dehydrogenation and dehydrocyclization that ensures the processing of not only hydroaromatics but also both alkanes and cycloalkanes to accomplish dehydrogenation of cyclo-C6-alkanes and alkanes dehydrocyclization.

This object is solved by the process of hydrocarbons dehydrogenation and dehydrocyclization which includes contacting feed flow over a catalyst based on a x-ray amorphous carbon such as that described above.

The temperature of the process is in the range of 350 to 600° C. and the pressure is in the range of 0.01 to 0.15 mPa. The contacting of flow of feed with catalyst can be realized at the supply of a feed with liquid hourly space velocity in the range of 0.1 to 10.0 $h^{-1}$.

In the claimed process a feed that can be used contains alkanes with carbon atoms number not less than 6.

Petroleum, a feed of reforming process including unstabilized alkenes, not removed by hydrogenation to alkanes, products of reforming process (catalysate) including those obtained after aromatics isolation (i.e. raffinate), can be used as the feed in the claimed process.

The claimed process of hydrocarbons dehydrogenation and dehydrocyclization includes the use of a catalyst based on x-ray amorphous carbon where the x-ray amorphous carbon is prepared by carbonic material evaporation and has the following characteristics: a starting temperature of an air oxidation $T_{so} \leqq 320°$ C.; a temperature of maximal rate of an air oxidation $T_{omr} \leqq 590°$ C.; a temperature of end of an air oxidation $T_{oe} \leqq 630°$ C.; an initial rate of hydrogenolysis at 700° C., in the absence of hydrogen activating catalyst, $V_{hin} \geqq 2.08\%$ mass of carbon/h; and a limiting amount of $MnO_4^-$ ions expendable at a contact with 1 g of named carbon in the solution $\geqq 16$ mmole.

Contacting of flow of feed is preferentially realized over catalyst based on x-ray amorphous carbon having temperature $T_{so}=280°$ C. and temperature $T_{omr}=508°$ C.

x-Ray amorphous carbon used in claimed process can have specific surface S=210 to 280 $m^2/g$ and bulk density $\rho \leqq 0.05$ $g/cm^3$. It can be prepared for example by carbonic material evaporation by the action of electric arc or laser radiation.

The catalyst can contain inert granular material composed of particles with size of 0.25 to 1.00 mm. Quartz or ceramics can be introduces as inert granular material.

x-Ray amorphous carbon and inert granular material can be taken in following proportion: x-ray amorphous carbon 1.65-99.00% by mass with the rest being inert granular material.

In the claimed process, the catalyst can be used in form of granules molded from a mixture of x-ray amorphous carbon and a binder.

Neutral gel of hydroxides of metal selected from a group consisting aluminum, magnesium, zirconium, titanium, hafnium or the mixture of neutral gels at least two hydroxides of metals selected from group referred above can be introduced as a binder.

Neutral hydrogel of metal selected from group indicated above or a mixture at least two neutral hydrogels or natural hydrogel can be introduced as a binder in the catalyst.

Granulated catalyst after molding is subjected to thermal treatment in vacuum at temperature range from 200 to 550° C.

In the claimed process x-ray amorphous carbon and a binder can be present in following proportion: x-ray amorphous carbon 1.65-40.00% by mass and binder the rest.

As described above, the catalyst used in the claimed process, independently of production technique, its reactivity and catalytic activity, contains by analysis 95-97% mass carbon, less than 1.0% hydrogen and 4-5% oxygen. Hydrogen and oxygen are present in the form of water that is difficult to remove, since water was detected in absolute methanol after washing of x-ray amorphous carbon that was vacuum-processed at 100° C. during 10 h. The content of hydrogen and oxygen do not exceed measurement error at the end of one cycle "deep vacuum at 150° C.—dry air adsorption".

The specific surface of the catalyst used in the claimed process is in the range of 210 to 280 $m^2/g$, depending on production conditions; for finely dispersed graphite, for comparison, this value is 6 $m^2/g$). If the catalyst is prepared at energy flow less than 50 $W/mm^2$ it can include unconverted graphite that is detected by slow mass loss at temperature higher than 670° C. and graphitized particles (not completely converted graphite) detectable by mass loss in the temperature range of 645-670° C. (see FIG. 1). Graphite also is determined by sharp line 002 in spectra of x-ray diffraction (see FIG. 2).

The presence of graphitized particles and graphite sharply decreases catalyst reactivity. The catalyst prepared by evaporation of carbonic material at the action of energy flow of 50 to 300 $W/mm^2$ and having high catalytic activity is essentially devoid of graphite and graphitized particles, as is evidenced by the absence of line 002 of graphite (see FIG. 2) and temperature of end of an air oxidation $T_{eo}=630°$ C. (see FIG. 1).

The ESR spectra of the catalyst in vacuum is represented by a single line with linewidth 0.19 mT and g-factor 2.0022 (see FIG. 3). This line is similar to Lorentzian curve in the centre and has wide wings. The catalyst contains $(2-5) \times 10^{20}$ spins on carbon moles, i.e. 1 paramagnetic center per 1000-3000 carbon atoms that is determined by second integral of ESR spectra (or area under integral form of line). The paramagnetic centers are defied by defects of the dangling C—C bonds type.

Besides dangling bonds, the catalyst contains non-conjugated multiple C=C bonds. Both these functional groups contribute in the reactivity of the catalyst and determine its catalytic activity.

As with similar compounds having non-conjugated multiple C=C bonds, x-Ray amorphous carbon interacts with $MnO_4^-$-ion in neutral media (Vagner test reaction) and is brominated by solution of $Br_2$ or $(C_4H_9)_4NBr_3$, but does not reacts with maleic anhydride. At a contact of x-ray amorphous carbon with $MnO_4^-$ ions in neutral solution, a decrease of $MnO_4^-$ ion concentration is observed and $MnO_4^-$ ion consumption in neutral media per 1 g of x-ray amorphous carbon exceed 16 mmoles. Other carbonic materials, in particular graphite, glassy carbon and activated carbons do not interact with $MnO_4^-$ ion, i.e. $MnO_4^-$ ion is not consumed at the contact with these other carbonic materials.

The concentration of detectable multiple C=C bonds is much higher than dangling ones and amounts, for the most active catalysis samples, to one double bond per 5 carbon atoms. The high reactivity of the catalyst used in the claimed process (anomalously low value of starting temperature and temperature of the end of an air oxidation, oxidation and bromination in a solution and hydrogenolysis, without use of activating hydrogen catalysts) points to the presence of non-conjugated multiple bonds, which are absent in the structure of other carbonic materials.

Dehydrogenation transformations of hydrocarbons over the present catalyst probably occur as reactions with hydrogen transfer, where an alkane is a hydrogen donor and the catalyst is hydrogen acceptor converted at dehydrogenation temperatures to relatively unstable hydride forms. This is quite reasonable since we show hydrogenolysis of present catalyst, in the absence of activating hydrogen catalysts, at temperatures $\geq 700°$ C.; however hydrogen chemisorption is not found to 400° C.

EXEMPLIFICATION

The following examples will serve to illustrate the method of preparation of catalyst x-ray amorphous carbon.

Example 1

Graphite rod with diameter 8 mm was evaporated in chamber with diameter 85 mm at its advance speed 1.0 mm/min, current 65 A and voltage 38.7 V (energy flow equals 50 W/mm$^2$) and helium pressure 100 Torr. Condensed fullerene soot was subjected to exhaustive extraction by toluene in Soxlet apparatus, washed by ether and dried off at 150° C. in vacuum to produce x-ray amorphous carbon (yield 60.5% based on evaporated carbon) that is characterized by starting temperature of an air oxidation $T_{so}=320°$ C.; temperature of maximal rate of an air oxidation $T_{omr}=590°$ C.; temperature of end of an air oxidation $T_{oe}=630°$ C.; limiting amount of $MnO_4^-$ ions expendable at a contact with 1 g of the carbon in the solution 20 mmole; hydrogenolysis by molecular hydrogen, without activating hydrogen catalysts, at temperature 700° C. with an initial rate 2.08% mass of carbon/h.

Example 2

Graphite rod with diameter 6.0 mm was evaporated in chamber with diameter 85 mm at its advance speed 6.0 mm/min, current 212 A and voltage 40 V (energy flow equals 300 W/mm$^2$) and helium pressure 700 Torr. Condensed fullerene soot underwent exhaustive extraction by toluene in Soxlet apparatus, washed by ether and dried off at 150° C. in vacuum to produce x-ray amorphous carbon (yield 90.5% based on evaporated carbon) with starting temperature of an air oxidation $T_{so}=280°$ C., temperature of maximal rate of an air oxidation $T_{omr}=508°$ C., temperature of end of an air oxidation $T_{oe}=630°$ C., limiting amount of $MnO_4^-$ ions consumed at contact with 1 g of the x-ray amorphous carbon in the solution of 24 mmole, subjected to hydrogenolysis by molecular hydrogen, without activating hydrogen catalysts, at temperature 700° C. with initial rate 2.22% mass of carbon/h.

Example 3

Graphite rod with diameter 10.0 mm was evaporated in chamber with diameter 85 mm at its advance speed 1.0 mm/min, current 55 A and voltage 40 V (energy flow equals 27.1 W/mm$^2$) and helium pressure 100 Torr. Condensed fullerene soot underwent exhaustive extraction by toluene in Soxlet apparatus, washed by ether and dried off at 150° C. in vacuum to produce x-ray amorphous carbon (yield 40.3% on evaporated carbon) with starting temperature of an air oxidation $T_{so}=360°$ C., temperature of maximal rate of an air oxidation $T_{omr}=590°$ C., temperature of end of an air oxidation $T_{oe}=690°$ C., limiting amount of $MnO_4^-$ ions expendable at a contact with 1 g of named carbon in the solution 10 mmole, does not undergo hydrogenolysis by molecular hydrogen without activating hydrogen catalysts at temperature 700° C.

The following examples will serve to illustrate the industrial application of the claimed catalyst.

Example 4

4.0 cm$^3$ of crushed quartz, plug of basalt yarn, fixed bed catalyst consisted of mechanical mixture of 0.05 g of x-ray amorphous carbon that is characterized by temperatures $T_{so}=320°$ C., $T_{omr}=580°$ C. and $T_{oe}=630°$ C., value $V_{hin}=2.1\%$ mass of carbon/h and limiting amount of $MnO_4^-$ ions expendable at a contact with 1 g of named carbon in the solution 16 mmole and 2.95 g of crushed quartz with particle size 0.25-0.5 mm (1.65% of x-ray amorphous carbon, 98.35% of inert granular material, total volume is 2.4 cm$^3$) in sequence were placed in a tubular flow reactor. The reactor was purged by argon for 0.5 h to remove air bottom-up and thermostatically controlled in argon flow at temperature of 550° C., then butane-butene fraction composed (in % mol.) of n-butane 23.5, iso-butane 10.3, butene-1 39.5, butene-2 8.7, i-butene 14.9, butadiene-1,3 1.6, $C_1$-$C_3$ hydrocarbons 0.3, $C_5$-$C_7$ hydrocarbons 0.9 was passed through reactor bottom-up with space velocity 40 cm$^3$/min (1000 h$^{-1}$). The output gas contained (in % mol.) n-butane 20.0, iso-butane 8.5, butene-1 21.1, butene-2 9.2, i-butene 14.2, butadiene-1,3 5.0, hydrocarbons $C_1$-$C_3$ 11.6, hydrocarbons $C_5$-$C_7$ 1.5, hydrogen 9.6. The conversion degree with respect to butanes was 15-17%; conversion degree of butene-1 was 46.0%.

Example 5

Fixed bed catalyst consisted of a mechanical mixture of 0.6 g of x-ray amorphous carbon that is characterized by temperatures $T_{so}=320°$ C., $T_{omr}=590°$ C. and $T_{oe}=630°$ C., value $V_{hin}=2.08\%$ mass of carbon/h and limiting amount of $MnO_4^-$ ions expendable at a contact with 1 g of named carbon in the solution 16 mmole and 2.4 g of crushed quartz with particle size 0.5-0.75 mm (2.0% of x-ray amorphous carbon, 98.0% of inert granular material, total volume is 2.4 cm$^3$), plug of basalt yarn and 5 cm$^3$ of crushed ceramic with particle size 0.75-1.00 mm were placed in a tubular flow reactor in sequence. The reactor was purged by argon for 0.5 h to remove air bottom-up and thermostatically controlled in argon flow at temperature of 550° C., then saturated vapours of n-hexane in argon at 22 C were passed through the reactor with space velocity 40 cm$^3$/min (1000 h$^{-1}$ on gas, 1 h$^{-1}$ on liquid n-hexane).

The hydrocarbonaceous product obtained contained (in % mol.): initial n-hexane 46.9, benzene 39.3, $C_6$ hydrocarbons 2.1, $C_5$ hydrocarbons 0.2, $C_4$ hydrocarbons 3.7, propene 3.0, propane 1.1, ethene 1.8 and methane 1.8. The conversion degree of initial n-hexane is 54.1%, selectivity on benzene was 72.6%, selectivity on isomerization products was 3.8%, selectivity on cracking products was 11.6%.

Example 6

Fixed bed catalyst in extrudate form 3 mm in diameter composed of mixture of 12.0 g of x-ray amorphous carbon that is characterized by temperatures $T_{so}=280°$ C., $T_{omr}=508°$ C. and $T_{oe}=630°$ C., value $V_{hin}=2.2\%$ mass. of carbon/h and limiting amount of $MnO_4^-$ ions consumed at a contact with 1 g of named carbon in the solution 16.6 mmole and 18.0 g of neutral aluminum hydroxide (40% of x-ray amorphous carbon, 60% of a binder, catalyst volume was 37.5 cm$^3$) and 50 cm$^3$ of crushed quartz with particle size 0.5-0.75 mm in sequence were placed in a tubular flow reactor. The reactor was purged bottom-up by argon for 0.5 h to remove air and thermostatically controlled in argon flow at temperature of 550° C., then n-octane with space velocity 37.5 ml/h (1 h$^{-1}$ on liquid n-octane) was passed. The reactor pressure was equal to 760 Torr (0.1 mPa). The hydrocarbonaceous part of products contained (in % mol.) initial n-octane 3.7, xylenes and ethylbenzene in total 56.8, toluene 4.8, benzene 2.0, $C_7$ hydrocarbons 19.3, $C_6$ hydrocarbons 5.8, $C_5$ hydrocarbons 1.2, $C_4$ hydrocarbons 3.9, propene 1.0, propane 0.6, ethene 0.2, ethane 0.6 and methane 0.14. The conversion degree of initial n-octane was 96.3%, selectivity on aromatics was 66.0%.

Example 7

In the conditions of example 3 over catalyst in the extrudate form 3 mm in diameter composed of 0.5 g of x-ray amorphous carbon that is characterized by temperatures $T_{so}$=290° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16.4 mmole, and 29.5 g of neutral titanium hydroxide (1.66% of x-ray amorphous carbon, 98.34% of binder, catalyst volume was 38 cm$^3$) and 50 cm$^3$ of earthenware rings feeds extractive gasoline (boiling range: 80-125 C, comprising (in % mol.) $C_6$ hydrocarbons 55, $C_7$ hydrocarbons 30, $C_8$ hydrocarbons 10) with space velocity equal to 114 ml/h (3 h$^{-1}$). The reactor pressure was equal to 760 Torr (0.1 mPa). Hydrocarbonaceous products of reaction contained (in % mol.), along with not converted initial hydrocarbons (in the total 44.5%): benzene 10.8, toluene 20.4, xylenes 15.5, cracking products in the total 5. The conversion degree of initial $C_6$-$C_8$ hydrocarbons was 54, 55 and 45%, respectively. The feed with RM octane number equal to 13 was converted to the product with RM octane number equal to 78.

Example 8

In the conditions of example 2 over catalyst composed of 3.0 g of x-ray amorphous carbon that is characterized by temperatures $T_{so}$=280° C., $T_{omr}$=508° C. and $T_{oe}$=630° C., value $V_{hin}$=2.08% mass. of carbon/h and limiting amount of $MnO_4^-$ ions expendable at a contact with 1 g of named carbon in the solution 16.6 mmole, and 0.03 g of crushed quartz with particle size 0.25-0.5 mm (99.0% of x-ray amorphous carbon, 1.0% of granular material) the saturated at 22 C vapors of n-pentane in argon with space velocity 2.0 cm$^3$/min (50 h$^{-1}$ on gas, 0.1 h$^{-1}$ on liquid n-pentane) were flowed through the reactor. The reactor pressure was equal to 760 Torr (0.1 mPa). The hydrocarbonaceous part of products contained (in % mol) initial n-pentane 83.4, benzene 5.8, pentane isomers 2.4, $C_4$ hydrocarbons 1.5, propene 2.8, propane 1.2, ethene 0.6, ethane 2.2 and methane 0.5. The conversion degree of initial n-pentane was 16.6%, selectivity on benzene was 34.9%, selectivity on isomerization products was 14.1%, selectivity on cracking products was 52.9%.

Example 9

In the conditions of example 2 at 550° C. 3.0 g of crushed quartzes as the catalyst was used. The hydrocarbonaceous part of products contained un-converted initial n-hexane only, i.e. quartz does not catalyze dehydrogenation, dehydrocyclization, cracking and isomerization of n-hexane at 550° C.

Example 10

In the conditions of example 33.0 g of extrudate 3 mm in diameter composed of neutral aluminum hydroxide as the catalyst was used. The saturated at 22 C vapours of n-heptane in argon were flowed through the reactor. The hydrocarbonaceous part of products contained (in % mol.) initial n-heptane 97.5, $C_6$ hydrocarbons 0.4, $C_5$ hydrocarbons 0.4, $C_4$ hydrocarbons 0.3, propane 0.5, ethene 0.7, ethane 0.1, methane 0.1. Conversion degree of initial n-heptane was equal 2.5%. Aromatics were absent, products with carbon atoms number less than 7, i.e. cracking products were present.

Example 11

In the conditions of example 2 at 550° C. mechanical composition consisted of 0.1 g of graphite and 2.9 g of crushed quartz as the catalyst was used. The hydrocarbonaceous part of products contained un-converted initial n-hexane only, i.e. graphite composed of carbon does not catalyze dehydrogenation, dehydrocyclization, cracking and isomerization of n-hexane at 550 C.

Example 12

In the conditions of example 3 to the reactor filled by the catalyst in extrudate form 3 mm in diameter composed of 6.0 g of x-ray amorphous carbon that is characterized by temperatures $T_{so}$=290° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16.3 mmole, and 24.0 g of neutral aluminum hydroxide (20.0% of x-ray amorphous carbon, 80.0% of a binder, catalyst volume is 38 cm$^3$) and 50 cm$^3$ of earthenware rings 4 mm in diameter and thermostatically controlled at 550° C. stabilized feed of reforming hydrogenate of straight-run gasoline with cut points 96-157° C. was fed with space velocity 114 ml/h (3 h$^{-1}$). The reactor pressure was equal 760 Torr (0.1 mPa). The hydrocarbonaceous part of products contained (in % mol.) $C_1$-$C_4$ hydrocarbons 12.4, $C_5$ hydrocarbons 3.9, $C_6$ hydrocarbons 4.5, $C_6$ hydrocarbons 4.0, benzene 3.8, toluene 28.2, xylenes and ethylbenzene in total 55.6. Liquid catalysate yield was equal 87.6%.

Example 13

0.1 g of fullerene $C_{60}$ is placed in quartz ampoule with capacity 50 cm$^3$. The ampoule was subjected to vacuum to residue pressure 0.01 Torr and the ampoule was charged by n-hexane vapor to pressure 100 Torr. The ampoule was soldered up and held in static conditions at 530° C. during 6 h. Gas test indicated 100 Torr of ethane and 200 Torr of ethene with both benzene and initial n-hexane absent, pointing to multiple n-hexane cracking over fullerene $C_{60}$.

Example 14

0.1 g of x-ray amorphous carbon that is characterized by temperatures $T_{so}$=280° C., $T_{omr}$=508° C. and $T_{oe}$=630° C., value $V_{hin}$=2.08% mass. of carbon/h and limiting amount of $MnO_4^-$ ions expendable at a contact with 1 g of named carbon in the solution 16.6 mmole, is placed in quartz ampoule with capacity 50 cm$^3$. A vacuum was pulled on the ampoule to residue pressure 0.01 Torr and the ampoule was charged by n-hexane vapor to pressure 100 Torr. The ampoule was soldered up and held in static conditions at 530° C. during 2 h. Gas sample was had, in addition to hydrogen, 23 Torr of starting n-hexane, 71 Torr of benzene, 3 Torr of ethene and 3 Torr of butane. Conversion degree of n-hexane was 77%, selectivity with respect to benzene was 92.2%, selectivity with respect to cracking products was 7.8%.

Example 15

In the conditions of example 2 mechanical composition consisted of 0.1 g of fullerene $C_{60}$ epoxide and 2.9 g of crushed quartz as the catalyst was used at 550° C. and saturated at 22 C vapors of n-hexane in argon was passed. The reactor pressure was equal 760 Torr (0.1 mPa). The hydrocarbonaceous part of products contained, in addition to un-converted n-hexane (43.7%), $C_1$-$C_5$ alkanes and $C_2$-$C_5$ alkenes, i.e. n-hexane conversion degree is equal 56.3% and selectivity with respect to cracking products was 100%.

Example 16

In the conditions of example 3 to the reactor filled by the catalyst in extrudate form 3 min in diameter composed of 10.0 g of x-ray amorphous carbon that is characterized by temperatures $T_{so}$=310° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16 mmole, and 20.0 g of neutral zirconium hydroxide (33.3% of x-ray amorphous carbon, 66.7% of a binder, catalyst volume is 38 cm$^3$) and 50 cm$^3$ of crushed quartz with particle size 0.75-1.00 mm and thermostatically controlled at 550° C. cyclohexane feed with space velocity 380 ml/h (10 h$^{-1}$). The reactor pressure was maintained to 1140 Torr (0.15 mPa) by means of needle valve. The hydrocarbonaceous part of reaction products contained (in % mol.) cyclohexane 5.5, benzene 91.1 and $C_6$ hydrocarbons 3.4. Cyclohexane conversion degree was 94.5%, selectivity with respect to dehydrogenation product benzene was equal 96.4%.

Example 17

In the conditions of example 3 to the reactor filled by the catalyst in extrudate form 3 mm in diameter composed of 6.0 g of x-ray amorphous carbon that is characterized by temperatures $T_{so}$=290° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16.4 mmole, and 24.0 g of neutral aluminum hydroxide (20.0% of x-ray amorphous carbon, 80.0% of a binder, catalyst volume is 38 cm$^3$) and 50 cm$^3$ of earthenware rings 4 mm in diameter and thermostatically controlled at 550° C. raffinate feed with cut points 80-142° C. and space velocity 114 ml/h (3 h$^{-1}$). The hydrocarbonaceous part of reaction products contained (in % mol.) $C_1$-$C_4$ hydrocarbons 22.7, $C_5$ hydrocarbons 0.5, $C_6$ hydrocarbons 0.4, $C_7$ hydrocarbons 0.5, benzene 29.3, toluene 14.0 and xylenes and ethylbenzene in total 0.4. Liquid catalysate yield was 77.4%.

Example 18

In the conditions of example 3 to the reactor filled by the catalyst in extrudate form 3 mm in diameter composed of 10.0 g of x-ray amorphous carbon that is characterized by temperatures $T_{so}$=310° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16 mmole, and 20.0 g of neutral zirconium hydroxide (33.3% of x-ray amorphous carbon, 66.7% of a binder, catalyst volume is 38 cm$^3$) and 50 cm$^3$ of crushed quartz with particle size 0.75-1.00 mm and at 600° C. cyclohexane feed with space velocity 380 ml/h (10 h$^{-1}$). The pressure in the reactor was 760 Torr (0.1 mPa). The hydrocarbonaceous part of reaction products contained (in % mol.) cyclohexane 3.5, benzene 88.1 and $C_6$ hydrocarbons 0.4. Cyclohexane conversion degree was 96.5%, selectivity with respect to dehydrogenation product benzene was equal to 91.3%.

Example 19

In the conditions of example 3 to the reactor filled by the catalyst in extrudate form 3 min in diameter composed of 10.0 g of x-ray amorphous carbon that is characterized by temperatures $T_{so}$=310° C., $T_{omr}$=520° C. and $T_{oe}$=630° C., value $V_{hin}$=2.08% mass. of carbon/h and limiting amount of $MnO_4^-$ ions expendable at a contact with 1 g of named carbon in the solution 16.1 mmole, and 20.0 g of neutral zirconium hydroxide (33.3% of x-ray amorphous carbon, 66.7% of a binder, catalyst volume is 38 cm$^3$) and 50 cm$^3$ of crushed quartz with particle size 0.75-1.00 min and at 350° C. was fed cyclohexane with space velocity 38 ml/h (1 h$^{-1}$). The pressure in the reactor is maintained at 76 Torr (0.01 mPa) by means of both manostat and water-jet pump. The hydrocarbonaceous part of reaction products contained (in % mol.) cyclohexane 20.2, benzene 66.5, $C_6$ hydrocarbons 0.2, C4 hydrocarbons 6.5 and $C_2$ hydrocarbons 6.6. Cyclohexane conversion degree was 79.8%, selectivity with respect to benzene was equal 83.4%.

What is claimed is:

1. A hydrocarbon conversion catalyst, comprising substantially fullerene-free X-ray amorphous carbon produced by a carbonic material evaporation, the substantially fullerene-free X-ray amorphous carbon having:
    an air oxidation starting temperature not higher than 320 degrees C.;
    an air oxidation final temperature not higher than 630 degrees C.;
    an air oxidation maximal rate temperature not higher than 590 degrees C.;
    an initial rate of non-catalytic hydrogenolysis by molecular hydrogen of at least 2.08 percent by mass of carbon per hour at 700 degrees C.; and
    consuming, in a solution, at least 16 mmoles of $(MnO_4)^-$ ions per gram of said carbon,
    wherein the substantially fullerene-free X-ray amorphous carbon is molded into granules or molded into granules with a binder or mixed with an inert granular material.

2. The hydrocarbon conversion catalyst of claim 1, wherein the air oxidation starting temperature is 280 degrees C.

3. The hydrocarbon conversion catalyst of claim 1, wherein the air oxidation maximal rate is 508 degrees C.

4. The hydrocarbon conversion catalyst of claim 1, wherein the X-ray amorphous carbon has a bulk density not greater than 0.05 g/cm$^3$.

5. The hydrocarbon conversion catalyst of claim 1, wherein the X-ray amorphous carbon has a specific surface in the range from 210 to 280 m$^2$/g.

6. The hydrocarbon conversion catalyst of claim 1, wherein the X-ray amorphous carbon is present in the catalyst in an amount of at least 1.65 mass percent.

7. The hydrocarbon conversion catalyst of claim 1, wherein the X-ray amorphous carbon is present in the catalyst in a mass percent amount in the range from 1.65% to 99.00%.

8. The hydrocarbon conversion catalyst of claim 1, further comprising a granular material.

9. The hydrocarbon conversion catalyst of claim 8, wherein the granular material is quartz or a ceramic material.

10. The hydrocarbon conversion catalyst of claim 9, wherein the granular material has a particle size in the range from 0.25 to 1.00 mm.

11. The hydrocarbon conversion catalyst of claim 1, wherein the X-ray amorphous carbon is molded with a binder.

12. The hydrocarbon conversion catalyst of claim 11, wherein the binder is selected from the group consisting of metal hydroxide neutral gel, metal neutral hydrogel and clay.

13. The hydrocarbon conversion catalyst of claim 12, wherein the metal in metal hydroxide or metal neutral hydrogel is selected from the group consisting of aluminum, zirconium, titanium and hafnium.

14. The hydrocarbon conversion catalyst of claim 12, wherein the x-ray amorphous carbon is present in the catalyst in a mass percent amount in the range from 1.65% to 40%.

15. The hydrocarbon conversion catalyst of claim 12, wherein the catalyst is subjected to calcination in vacuum at a temperature in the range from 200 to 550 degrees C.

16. A method for producing substantially fullerene-free X-ray amorphous carbon catalyst for hydrocarbon conversion having:
   an air oxidation starting temperature not higher than 320 degrees C.;
   an air oxidation final temperature not higher than 630 degrees C.;
   an air oxidation maximal rate temperature not higher than 590 degrees C.; and
   an initial rate of non-catalytic hydrogenolysis by molecular hydrogen, at 700 degrees C., of at least 2.08 percent by mass of carbon per hour, wherein, a gram of said carbon, in a solution, consumes an amount of at least 16 mmoles of $(MnO_4)^-$ ions,
   the method comprising:
   evaporating a carbonic material in a helium atmosphere using energy flow in the range from 50 to 300 $W/mm^2$;
   removing fullerenes from soot using a solvent, thereby producing the substantially fullerene-free X-ray amorphous carbon as insoluble residue; and
   molding the substantially fullerene-free X-ray amorphous carbon into granules or molding the substantially fullerene-free X-ray amorphous carbon into granules with a binder or mixing the substantially fullerene-free X-ray amorphous carbon with an inert granular material.

17. The method of claim 16, wherein fullerenes are removed from soot by organic solvent extraction.

18. The method of claim 17, wherein the organic solvent extraction is followed by washing and drying.

19. The method of claim 18, wherein drying is conducted in vacuum at a temperature in the range of from 150 degrees C. to 200 degrees C.

20. The method of claim 16, wherein the carbonic material is graphite.

21. The method of claim 16, wherein the carbonic material is evaporated by electric arc discharge, laser or ultrahigh frequency radiation in a chamber with coaxial electrodes.

22. The method of claim 21, wherein the carbonic material is evaporated by electric arc discharge in a chamber with coaxial electrodes, wherein at least one electrode is formed from graphite, has a positive polarity and is advanced toward a second electrode at a rate in the range from 0.2 to 6 mm/minute.

23. The method of claim 16, wherein the helium atmosphere has a pressure in the range from 100 to 760 Torr.

24. A process for producing a hydrocarbon conversion catalyst, comprising combining the X-ray amorphous carbon produced by the method of claim 16, with a granular material.

25. A process for producing a hydrocarbon conversion catalyst, comprising molding the X-ray amorphous carbon produced by the method of claim 16, with a binder.

26. A hydrocarbon conversion process, comprising:
   contacting a hydrocarbon feed with substantially fullerene-free X-ray amorphous carbon produced by carbonic material evaporation having:
   an air oxidation starting temperature not higher than 320 degrees C.;
   an air oxidation final temperature not higher than 630 degrees C.;
   an air oxidation maximal rate temperature not higher than 590 degrees C.;
   an initial rate of non-catalytic hydrogenolysis by molecular hydrogen, at 700 degrees C., of at least 2.08 percent by mass of carbon per hour, and wherein, a gram of said carbon, in a solution, consumes an amount of at least 16 mmoles of $(MnO_4)^-$ ions,
   thereby converting at least a portion of said hydrocarbon feed,
   wherein the substantially fullerene-free X-ray amorphous carbon is molded into granules or molded into granules with a binder or mixed with an inert granular material.

27. The process of claim 26, wherein the X-ray amorphous carbon is combined with a granular material or molded with a binder.

28. The process of claim 26, wherein the hydrocarbon feed includes an alkane, a cycloalkane or any combination thereof.

29. The process of claim 26, wherein the hydrocarbon feed includes petroleum.

30. The process of claim 26, wherein the hydrocarbon feed includes a reformate or a raffinate.

* * * * *